(12) United States Patent
Cheung et al.

(10) Patent No.: US 9,996,677 B2
(45) Date of Patent: Jun. 12, 2018

(54) SYSTEM AND METHOD FOR OBTAINING AN OBJECTIVE MEASURE OF DYSPNEA

(75) Inventors: Amy Oi Mee Cheung, Eindhoven (NL); Maryam Atakhorrami, Cambridge (GB)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1514 days.

(21) Appl. No.: 13/583,072

(22) PCT Filed: Feb. 14, 2011

(86) PCT No.: PCT/IB2011/050611
§ 371 (c)(1),
(2), (4) Date: Sep. 6, 2012

(87) PCT Pub. No.: WO2011/110963
PCT Pub. Date: Sep. 15, 2011

(65) Prior Publication Data
US 2012/0330114 A1    Dec. 27, 2012

Related U.S. Application Data

(60) Provisional application No. 61/311,434, filed on Mar. 8, 2010.

(51) Int. Cl.
*A61B 5/00* (2006.01)
*G06F 19/00* (2018.01)
(Continued)

(52) U.S. Cl.
CPC ........ *G06F 19/3487* (2013.01); *A61B 5/0816* (2013.01); *A61B 5/1118* (2013.01);
(Continued)

(58) Field of Classification Search
CPC combination set(s) only.
See application file for complete search history.

(56) References Cited

U.S. PATENT DOCUMENTS 5,582,182 A * 12/1996 Hillsman ............... A61B 5/087
600/529
5,645,053 A * 7/1997 Remmers et al. ........ 128/204.23
(Continued)

FOREIGN PATENT DOCUMENTS

CN        1897872 A      1/2007
WO    WO2005004986 A1   1/2005
(Continued)

OTHER PUBLICATIONS

Rosdahl, C.B. et al., "Difficult Breathing (Dyspnea)" Textbook of Basic Nursing, 9th Edition, Jan. 1, 2008, Lippincott Williams & Wilkns, XP055386553, pp. 522-523.

*Primary Examiner* — John R Downey
*Assistant Examiner* — Shirley Jian
(74) *Attorney, Agent, or Firm* — Michael W. Haas

(57) ABSTRACT

A computer-implemented method for assessing a level of dyspnea in a patient is provided. The method includes measuring physical activity of the patient over a period of time with an activity monitor to gather physical activity data; measuring respiration rate of the patient over the period of time with a respiration rate sensor to gather respiration rate data; administering a questionnaire to gather clinical information of the patient; and executing, on one or more computer processors, one or more computer program modules to determine a dyspnea value for the patient based on the respiration rate data, the physical activity data, and the clinical information of the patient. The dyspnea value is representative of the level of dyspnea in the patient.

21 Claims, 3 Drawing Sheets

(51) Int. Cl.
*A61B 5/08* (2006.01)
*A61B 5/11* (2006.01)
*A61B 5/113* (2006.01)
*A61B 7/00* (2006.01)

(52) U.S. Cl.
CPC ............ *A61B 5/681* (2013.01); *A61B 5/6804* (2013.01); *A61B 5/6831* (2013.01); *G06F 19/345* (2013.01); *G06F 19/363* (2013.01); *A61B 5/1135* (2013.01); *A61B 5/6824* (2013.01); *A61B 7/003* (2013.01)

(56) References Cited

U.S. PATENT DOCUMENTS

| | | | |
|---|---|---|---|
| 6,159,147 A | 12/2000 | Lichter | |
| 6,881,192 B1* | 4/2005 | Park | 600/529 |
| 6,889,691 B2* | 5/2005 | Eklund et al. | 128/204.21 |
| 7,680,534 B2* | 3/2010 | Hopper | A61N 1/3627 607/9 |
| 7,775,983 B2* | 8/2010 | Zhang | A61B 5/0816 600/481 |
| 7,993,280 B2* | 8/2011 | Zhang | A61B 5/0816 600/484 |
| 8,301,252 B2* | 10/2012 | Hatlestad | A61B 5/0031 607/17 |
| 8,319,648 B2* | 11/2012 | Siejko | A61B 5/0002 340/286.06 |
| 8,496,596 B2* | 7/2013 | Hatlestad | A61B 5/0809 600/484 |
| 8,515,535 B2* | 8/2013 | Hopper | A61N 1/3627 607/19 |
| 8,750,992 B2* | 6/2014 | Hopper | A61N 1/3627 607/9 |
| 8,928,671 B2* | 1/2015 | Adler | A61B 5/0022 345/473 |
| 8,954,146 B2* | 2/2015 | Hopper | A61N 1/3627 607/9 |
| 8,998,821 B2* | 4/2015 | Hatlestad | A61B 5/0809 600/529 |
| 9,277,885 B2* | 3/2016 | Hopper | A61N 1/3627 |
| 9,351,647 B2* | 5/2016 | Zhang | A61B 5/0205 |
| 2004/0111041 A1* | 6/2004 | Ni et al. | 600/544 |
| 2004/0116784 A1* | 6/2004 | Gavish | A61B 5/0205 600/300 |
| 2004/0138719 A1* | 7/2004 | Cho et al. | 607/42 |
| 2004/0200472 A1* | 10/2004 | Gold | 128/200.24 |
| 2005/0061320 A1* | 3/2005 | Lee et al. | 128/204.18 |
| 2005/0076909 A1* | 4/2005 | Stahmann | A61B 5/0031 128/204.23 |
| 2005/0081847 A1* | 4/2005 | Lee et al. | 128/200.24 |
| 2005/0085738 A1* | 4/2005 | Stahmann et al. | 600/529 |
| 2005/0148897 A1* | 7/2005 | Cho et al. | 600/533 |
| 2005/0209511 A1* | 9/2005 | Heruth et al. | 600/301 |
| 2005/0209512 A1* | 9/2005 | Heruth et al. | 600/301 |
| 2005/0209513 A1* | 9/2005 | Heruth et al. | 600/301 |
| 2005/0222503 A1* | 10/2005 | Dunlop et al. | 600/323 |
| 2006/0009708 A1* | 1/2006 | Rapoport et al. | 600/538 |
| 2006/0106275 A1* | 5/2006 | Raniere | 600/26 |
| 2006/0212081 A1 | 9/2006 | Suga | |
| 2006/0241708 A1* | 10/2006 | Boute | 607/17 |
| 2006/0293608 A1* | 12/2006 | Rothman et al. | 600/545 |
| 2007/0015976 A1* | 1/2007 | Miesel et al. | 600/301 |
| 2007/0032733 A1* | 2/2007 | Burton | 600/509 |
| 2007/0055115 A1* | 3/2007 | Kwok et al. | 600/300 |
| 2007/0083079 A1* | 4/2007 | Lee et al. | 600/27 |
| 2007/0123758 A1* | 5/2007 | Miesel et al. | 600/301 |
| 2007/0196780 A1* | 8/2007 | Ware | G09B 23/285 432/262 |
| 2007/0249952 A1* | 10/2007 | Rubin et al. | 600/544 |
| 2007/0276270 A1 | 11/2007 | Tran | |
| 2008/0009685 A1* | 1/2008 | Kim et al. | 600/300 |
| 2008/0033304 A1* | 2/2008 | Dalal et al. | 600/484 |
| 2008/0039730 A1* | 2/2008 | Pu et al. | 600/484 |
| 2008/0066753 A1* | 3/2008 | Martin et al. | 128/204.23 |
| 2008/0071150 A1* | 3/2008 | Miesel et al. | 600/301 |
| 2009/0078258 A1* | 3/2009 | Bowman et al. | 128/204.26 |
| 2010/0073170 A1* | 3/2010 | Siejko | A61B 5/0002 340/573.1 |
| 2010/0076333 A9* | 3/2010 | Burton et al. | 600/544 |
| 2011/0192400 A9* | 8/2011 | Burton et al. | 128/204.23 |
| 2012/0127157 A1* | 5/2012 | Adler | A61B 5/0022 345/419 |
| 2012/0130201 A1* | 5/2012 | Jain | A61B 5/08 600/301 |
| 2012/0130202 A1* | 5/2012 | Jain | A61B 5/0002 600/301 |
| 2012/0130203 A1* | 5/2012 | Stergiou | A61B 5/0002 600/301 |
| 2012/0197621 A1* | 8/2012 | Jain | G06F 19/3418 703/11 |
| 2012/0197622 A1* | 8/2012 | Jain | G06F 19/3418 703/11 |
| 2014/0155714 A1* | 6/2014 | Gavish | A61B 5/0205 600/324 |

FOREIGN PATENT DOCUMENTS

| | | |
|---|---|---|
| WO | WO2007052108 A2 | 5/2007 |
| WO | WO2007064682 A1 | 6/2007 |

* cited by examiner

SYSTEM AND METHOD FOR OBTAINING AN OBJECTIVE MEASURE OF DYSPNEA

CROSS-REFERENCE TO RELATED APPLICATIONS

This patent application claims the priority benefit under 35 U.S.C. § 371 of international patent application no. PCT/IB2011/050611, filed Feb. 14, 2011, which claims the priority benefit under 35 U.S.C. § 119(e) of U.S. Provisional Application No. 61/311,434 filed on Mar. 8, 2010, the contents of which are herein incorporated by reference.

BACKGROUND OF THE INVENTION

1. Field of the Disclosure

The present invention relates to a method and a system for assessing a level of dyspnea in a patient.

2. Description of the Related Art

Chronic Obstructive Pulmonary Disease (COPD) is a respiratory disease that is characterized by inflammation of the airways. It is characterized by an airflow limitation that is typically not fully reversible. The airflow limitation is both progressive and associated with an abnormal inflammatory response of the lungs to noxious particles or gases. Symptoms of COPD may include coughing, wheezing, dyspnea (i.e., shortness of breath or breathlessness), and the production of mucus and the degree of severity may, in part, be viewed in terms of the volume and color of secretions.

Dyspnea (i.e., shortness of breath or breathlessness) is one the most common symptom for COPD or Heart Failure (HF) patients. The worsening of dyspnea is an important indicator for the deterioration of health status of COPD or HF patient. Therefore, measurement of dyspnea provides valuable information for assessing the health status of COPD or HF patient.

Currently, dyspnea is measured using questionnaires. One such (most widely used) questionnaire is the Medical Research Council (MRC) questionnaire. The MRC questionnaire, which is shown in Table 1 below, is a five point scale questionnaire that allows patients to indicate the extent to which their breathlessness affects their daily activities. However, the MRC questionnaire does not quantify breathlessness itself and only provides a measure of perception of dyspnea by the patient. The perception of dyspnea is variable from patient to patient, as some patients may underestimate their level of dyspnea while other patients may overestimate their level of dyspnea.

TABLE 1

| MRC questionnaire | |
| --- | --- |
| Scale | Severity |
| 1 | Breathless with strenuous exercise |
| 2 | Short of breath when hurrying on the level surface or walking up a slight hill |
| 3 | Walks slower than people of the same age on a level surface because of breathlessness of I have to stop or I have to stop for breath when walking at my own pace on the level surface |
| 4 | Stops for breath after walking for 100 meters or a few minutes on a level surface |
| 5 | Too breathless to leave the house or I am breathless dressing and undressing |

Further, the questionnaire based assessments, such as one used for dyspnea, are subjective and rely on memory recall, which is especially difficult for the elderly. Also, the questionnaire based assessments, such as one used for dyspnea, are designed to be short (i.e., with specific questions/statements) to ensure compliance, but such short questionnaires may lack sensitivity to detect changes in the level of dyspnea. Furthermore, the questionnaire based assessments, such as one used for dyspnea, are unable to provide an accurate assessment of dyspnea, as these questionnaires do not account for a modification in behavior of the patient (e.g., patient may walk less to avoid getting breathless) and variation in effort provided by the patient (e.g., slow walking vs. fast walking).

SUMMARY OF THE INVENTION

One aspect of the present invention provides a computer-implemented method for assessing a level of dyspnea in a patient is provided. The method includes measuring physical activity of the patient over a period of time with an activity monitor to gather physical activity data; measuring respiration rate of the patient over the period of time with a respiration rate sensor to gather respiration rate data; administering a questionnaire to gather clinical information of the patient; and executing, on one or more computer processors, one or more computer program modules to determine a dyspnea value for the patient based on the respiration rate data, the physical activity data, and the clinical information of the patient. The dyspnea value is representative of the level of dyspnea in the patient.

Another aspect of the present invention provides a system for assessing a level of dyspnea in a patient. The system includes at least one sensor, a questionnaire system, and at least one processor. The sensor is configured to measure a) a respiration rate of the patient to gather respiration rate data; and b) physical activity of the patient to gather physical activity data. The questionnaire system is configured to gather clinical information of the patient. The processor is configured to process the respiration rate data, the physical activity data, and the clinical information of the patient to determine a dyspnea value for the patient. The dyspnea value is representative of the level of dyspnea in the patient.

Another aspect of the present invention provides a system for assessing a level of dyspnea in a patient. The system includes means for measuring physical activity of the patient over a period of time with an activity monitor to gather physical activity data; means for measuring respiration rate of the patient over the period of time with a respiration rate sensor to gather respiration rate data; means for administering a questionnaire to gather clinical information of the patient; and means for executing, on one or more computer processors, one or more computer program modules to determine a dyspnea value for the patient based on the respiration rate data, the physical activity data, and the clinical information of the patient. The dyspnea value is representative of the level of dyspnea in the patient.

These and other aspects of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. It shall also be appreciated that the features of one embodiment disclosed herein may be used in other embodi-

DETAILED DESCRIPTION OF EXEMPLARY EMBODIMENTS

Figure 1:
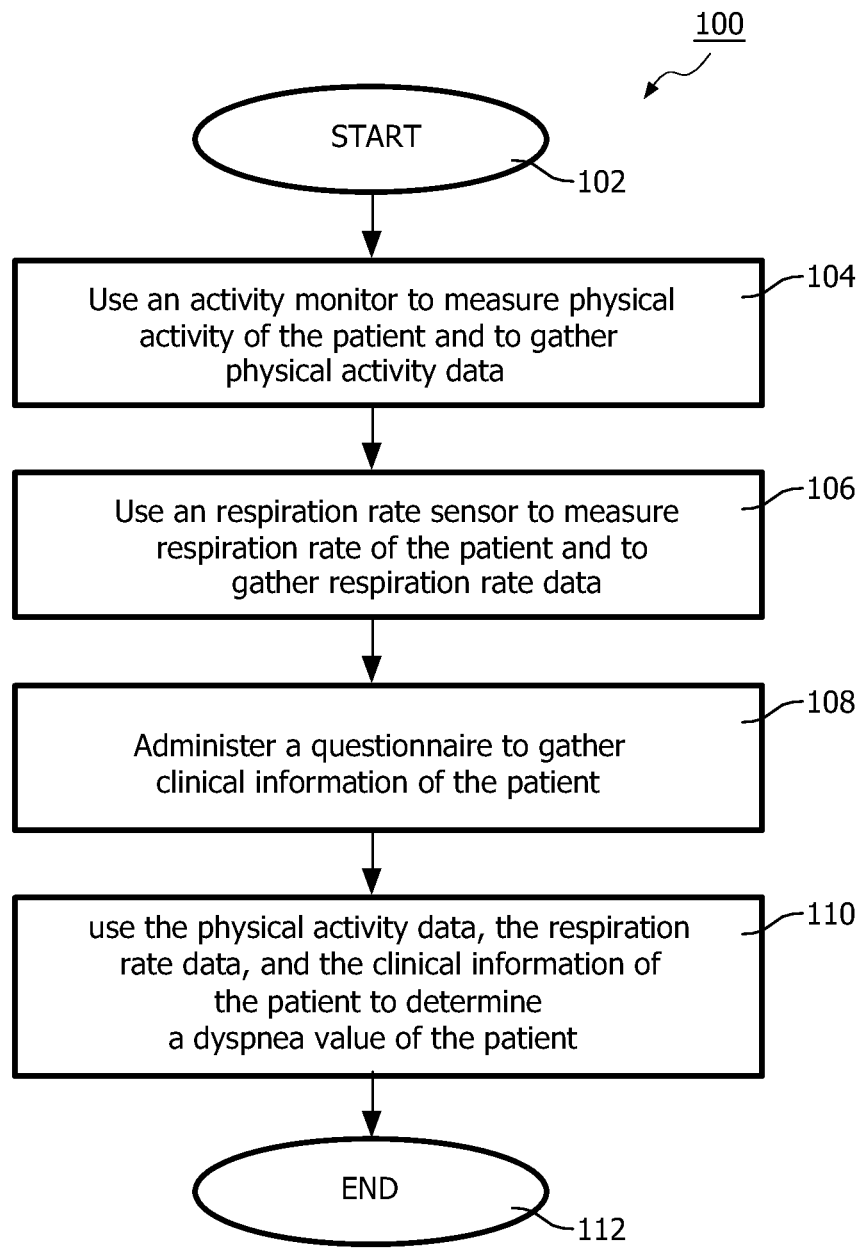
FIG. 1 is a flow chart illustrating a method for assessing a level of dyspnea in a patient in accordance with an embodiment of the present invention.

FIG. 1 is a flow chart illustrating a computer implemented method 100 for assessing a level of dyspnea in a patient in accordance with an embodiment of the present invention. Method 100 is implemented in a computer system comprising one or more processors 208 (as shown in and explained with respect to FIG. 2) or 308 (as shown in and explained with respect to FIG. 3) configured to execute one or more computer programs modules. In one embodiment, processor 208 (as shown in and explained with respect to FIG. 2) or 308 (as shown in and explained with respect to FIG. 3), each can comprise either one or a plurality of processors therein.

The computer implemented method 100 uses a combination of physical activity monitoring, respiration rate monitoring and questionnaires to provide a reliable measure of dyspnea. In one embodiment, as will be explained in detail below, the assessment of dyspnea is performed using a scoring card combining the different objective measurement inputs (i.e., physical activity data and respiration rate data) and subjective measurement inputs (clinical information of the patient obtained from the questionnaires) to output a dyspnea value representing the level of dyspnea in the patient.

In one embodiment, method 100 (and systems 200 or 300 described below) is configured to provide some objectivity to dyspnea measurement by integrating the three different inputs (the respiration rate data, the physical activity data and the clinical information of the patient from the questionnaire) for assessing the level of dyspnea. The method 100 (and systems 200 or 300 described below) also distinguishes if patients are underestimating or overestimating their perception of dyspnea as data related to their physical activity and respiration rate provide additional information necessary for evaluation of dyspnea.

For example, in one embodiment, if a patient scores a low value on the MRC questionnaire, yet has a low value on measured physical activity and a high value on measured respiration rate, then method 100 (and systems 200 or 300 described below) indicates that the patient is underestimating his/her dyspnea and that his/her perceived low level of dyspnea is possibly due to the fact, for example, that he/she is performing fewer physical activities.

The computer implemented method 100 begins at procedure 102. At procedure 104, a physical activity of the patient is measured over a period of time to gather physical activity data. The physical activity of the patient is measured over a period of time using an activity monitor, such as sensor 202 (as shown in and explained with respect to FIG. 2) or sensor 302 (as shown in and explained with respect to FIG. 3). In one embodiment, the physical activity is measured in arbitrary acceleration units (AAU).

At procedure 106, a respiration rate of the patient is measured over the period of time to gather respiration rate data. The respiration rate of the patient is measured over the period of time using a respiration rate sensor, such as sensor 204 (as shown in and explained with respect to FIG. 2) or sensor 302 (as shown in and explained with respect to FIG. 3). The respiration rate is generally representative of number of breaths taken by a patient per minute.

In one embodiment, the period of time may include a day, a week, a month, or any other desired time period. In one embodiment, the physical activity data and the respiration rate data are measured continuously over a period of time (e.g., three days) to provide an accurate estimate of average physical activity and average respiration rate of the patient.

Figure 2:
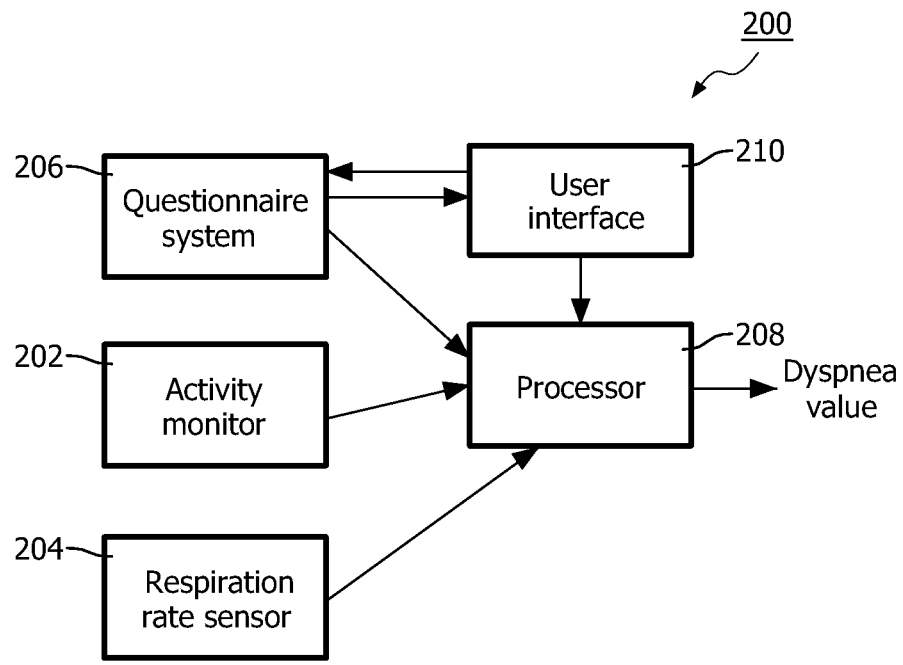
FIG. 2 shows a system for assessing the level of dyspnea in the patient in accordance with an embodiment of the present invention.
Figure 3:
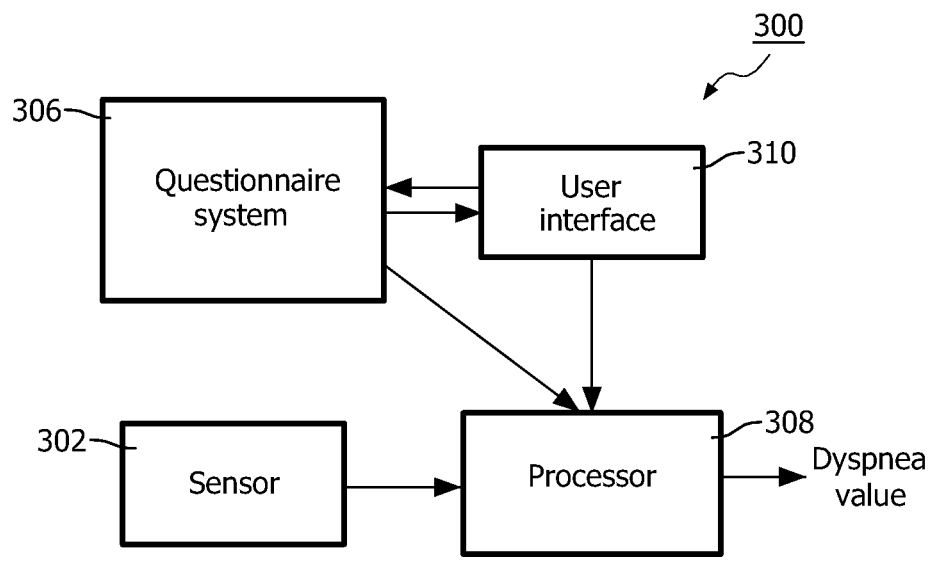
FIG. 3 shows a system for assessing the level of dyspnea in the patient in accordance with another embodiment of the present invention.

In one embodiment, as illustrated in FIG. 2, each of the physical activity, and the respiration rate of the patient may be measured (i.e., over the period of time) using separate sensors. In another embodiment, as shown in FIG. 3, a single sensor, such as the sensor 302, may be used measure both the physical activity and the respiration rate of the patient (i.e., over the period of time).

At procedure 108, clinical information of the patient is gathered by a questionnaire system 206. In other words, questionnaire system 206 is configured to administer a questionnaire to gather the clinical information of the patient. In one embodiment, the questionnaire may include one or more questions and responses to those questions. In one embodiment, the responses to the questions in the questionnaire provides the clinical information of the patient. In one embodiment, a patient (or a healthcare personnel) may input (e.g., manually) the clinical information into questionnaire system 206 using an user interface 210 (as shown in and described with reference to FIG. 2).

In one embodiment, the clinical information may include information about respiratory symptoms of the patient, information about smoking history of the patient, and information about any other illnesses of the patient. In one embodiment, the respiratory symptoms may include cough, phlegm, breathlessness, wheezing and chest illnesses.

In one embodiment, the clinical information of the patient is received by one or more processors 208 from questionnaire system 206. At procedure 110, processor 208 (as shown in and explained with respect to FIG. 2) or 308 (as shown in and explained with respect to FIG. 3) is configured to use the respiration rate data, the physical activity data, and the clinical information of the patient to determine a dyspnea value of the patient. In other words, the data from the questionnaire and various sensors are subsequently converted to the dyspnea value to provide an objective and continuous measure of the level of dyspnea in the patient. The method 100 ends at procedure 112.

In one embodiment, the procedures 102-112 can be performed by one or more computer program modules that can be executed by one or more processors 208 (as shown in and explained with respect to FIG. 2) or 308 (as shown in and explained with respect to FIG. 3).

The system 200 for assessing a level of dyspnea in a patient in accordance with an embodiment of the present invention is shown in FIG. 2. In one embodiment, system 200 of the present invention may be used by patients in the home environment of the patient. In another embodiment, the system 200 of the present invention may be used by a healthcare provider at a healthcare provider's location.

The system 200 may include activity monitor 202, the respiration rate sensor 204, questionnaire system 206, processor 208, and user interface 210.

In one embodiment, respiration rate sensor 204 and activity monitor 202 may provide an objective measure of the severity of dypsnea. In one embodiment, based on the obtained measurements (i.e., the monitored respiration rate, and/or the monitored activity level), a score card is used to classify the patient into either a safe category, at risk category or action required category.

Activity monitor 202 is configured to detect body movements of the patient such that a signal from activity monitor 202 is correlated to the level of a patient's physical activity. In one embodiment, activity monitor 202 may include an accelerometer. In one embodiment, the accelerometer may be a three-axis accelerometer. Such an accelerometer may include a sensing element that is configured to determine acceleration data in at least three axes. For example, in one embodiment, the three-axis accelerometer may be a three-axis accelerometer (i.e., manufacturer part number: LIS3L02AQ) available from STMicroelectronics.

In one embodiment, the output of the accelerometer may be represented in arbitrary acceleration units (AAU) per minute. The AAU can be related to total energy expenditure (TEE), activity-related energy expenditure (AEE) and physical activity level (PAL).

In another embodiment, the activity monitor 202 may be a piezoelectric sensor. The piezoelectric sensor may include a piezoelectric element that is sensitive to body movements of the patients.

In one embodiment, activity monitor 202 may be positioned, for example, at the thorax of the patient or at the abdomen of the patient. In one embodiment, activity monitor 202 may be a part of a wearable band (that may be worn on the wrist, waist, arm or any other portion of the patient's body for example) or may be part of wearable garment worn by the patient.

In one embodiment, respiration rate sensor 204, which is configured to measure the respiration pattern of the patient, may include an accelerometer or a microphone. In one embodiment, the accelerometer may be a three-axis accelerometer. For example, in one embodiment, the three-axis accelerometer may be a three-axis accelerometer available from STMicroelectronics.

In one embodiment, a microphone is constructed and arranged to receive sound of inspiration of the patient in order to determine the respiration rate of the patient.

In one embodiment, respiration rate sensor 204 may be a Respiband™ available from Ambulatory Monitoring, Inc. of Ardsley, N.Y. In one embodiment, Respiband™ measures the respiration rate using inductance.

In one embodiment, the respiration rate sensor may include a chest band and a microphone as described in U.S. Pat. No. 6,159,147, hereby incorporated by reference. In such an embodiment, the chest band may be placed around a patient's chest to measure the patient's respiration rate, for example. Sensors on the chest band may measure movement of the patient's chest. Data from sensors on the chest band is input into a strain gauge and subsequently amplified by an amplifier.

In one embodiment, questionnaire system 206 is configured to administer a questionnaire to gather the clinical information of the patient. In one embodiment, the questionnaire may include one or more questions and the patient's responses to those questions. In one embodiment, the responses to the questions in the questionnaire provide the clinical information of the patient. In one embodiment, the clinical information may include information about respiratory symptoms of the patient, information about smoking history of the patient, and/or information about any other illnesses of the patient. In one embodiment, the respiratory symptoms may include cough, phlegm, breathlessness, wheezing and/or chest illnesses.

In one embodiment, questionnaire system 206 is configured to perform the function of gathering the responses to the questions presented in the questionnaire. In one embodiment, questionnaire system 206 may include a data storage unit or memory that may be configured to store the questions of the questionnaire and to store the responses received in response to those questions. In one embodiment, the data storage unit or memory is a standalone device. However, it is contemplated that the data storage unit or memory may be part of questionnaire system 206.

In one embodiment, questionnaire system 206 is configured to retrieve questions (i.e., of the questionnaire) from the data storage unit or memory and to display the contents (i.e., questions and reply choices) of the questionnaire to the patient on user interface 210. In one embodiment, questionnaire system 206 is configured to gather responses to the questions in the questionnaire supplied by the patient using the user interface 210 and to store these responses in the data storage unit or memory. In one embodiment, the patient (or care provider) may manually input responses (i.e., the clinical information of the patient) to the questions in the questionnaire into questionnaire system 206 using user interface 210 (as shown in and described with reference to FIG. 2).

In one embodiment, the questions of the questionnaire, for example, in MRC questionnaire, are in the form of scaled questions, where responses are graded (e.g., severity of breathlessness of a patient on a scale of 1 to 5, with 5 being the most breathless). In another embodiment, the questions of the questionnaire may be in the form of multiple choice questions, where a response may be chosen from multiple options presented. In another embodiment, the questions of the questionnaire may be in the form of "yes/no" questions, where the response may be a "yes" or a "no."

In one embodiment, questionnaire system 206 may be configured to store one or more types of dyspnea questionnaires, for example, the Medical Research Council MRC scale questionnaire, the self-administered computerized (SAC) versions of the baseline dyspnea index (BDI) and transition dyspnea index (TDI), and the University of California San Diego (UCSD) Shortness of Breath Questionnaire (SOBQ). In such an embodiment, the healthcare personnel may select the type of dyspnea questionnaire that may be administered to gather the clinical information of the patient.

In one embodiment, questionnaire system 206 is configured to send the stored responses (i.e., clinical information of the patient) to one or more processors 208. In one embodiment, processor 208 can comprise either one or a plurality of processors therein. In one embodiment, the processor can be a part of or forming a computer system.

Processor 208 is configured to a) receive the physical activity data from activity monitor 202; b) receive the respiration data from respiration rate sensor 204; and c) receive the clinical information of the patient from questionnaire system 206; and d) process the respiration rate data, the physical activity data, and the clinical information of the patient to determine the dyspnea value for the patient. The dyspnea value is representative of the level of dyspnea in the patient.

In one embodiment, processor 208 is configured to assess the level of dyspnea using a scoring card combining the different objective measurement inputs (physical activity data and respiration rate data) and subjective measurement inputs (clinical information of the patient) to output a value representing the level of dyspnea. TABLE 2 shown below provides an exemplary integrated dyspnea scoring card. In one embodiment, processor 208 may include a data storage unit or memory (not shown) that is constructed and arranged to store the exemplary dyspnea scoring card.

TABLE 2

Exemplary dyspnea scoring card

| Questionnaire (e.g., MRC Questionnaire) | 1 | 2 | 3 | 4 | 5 |
|---|---|---|---|---|---|
| Respiration rate of the patient (breaths/min) | Low (<10) | Moderate (10-20) | | High >20 | |
| Physical Activity of the patient (arbitrary acceleration units (AAU)) | | High | | Moderate | Low |

In the illustrated embodiment, as shown in Table 2, the Medical Research Council MRC scale questionnaire is used to gather clinical information of the patient, however, it is contemplated that other types of dyspnea questionnaires, for example, the self-administered computerized (SAC) versions of the baseline dyspnea index (BDI) and transition dyspnea index (TDI), or the University of California San Diego (UCSD) Shortness of Breath Questionnaire (SOBQ) may be used.

In one embodiment, to obtain a more reliable quantification of dyspnea, processor 208 may be configured to use two baseline parameters to determine the dyspnea value. These two baseline parameters may include respiration rate at rest and respiration rate during activity. These two baseline parameters provide patient calibration as respiration rates may vary from patient to patient. The inclusion of these two baseline parameters to determine the dyspnea value enables some smart decision making in addition to the dyspnea scoring card described above.

For example, in one embodiment, the respiration rate at rest is equal to X, the respiration rate during activity is equal to Y, and the measured respiration rate is equal to Z. In one embodiment, if a) the measured respiration rate Z is greater than a sum of the respiration rate at rest X and a value of 10, and b) the physical activity of the patient is low, then the processor 208 of the system 200 is configured to determine that the patient is having a high level of dyspnea (i.e., patient is experiencing dyspnea). This condition is shown in Equation 1 below.

If $\{Z>(X+10)\}$ and physical activity of patient is low→patient is experiencing dyspnea. (Equation 1)

In one embodiment, if 1) the measured respiration rate Z lies between a) a sum of the respiration rate during activity Y and a value of 5, and b) a difference between the respiration rate during activity Y and a value of 5, and 2) the physical activity of the patient is low, then the processor 208 of the system 200 is configured to determine that the patient is not experiencing dyspnea (i.e., patient is performing normal physical activity). This is shown in Equation 2 below.

If $\{(Y-5)<Z<(Y+5)\}$ and physical activity of patient is high→patient is performing activity (Equation 2)

In one embodiment, the data storage unit or memory (not shown) of the processor 208 is constructed and arranged to receive and store the physical activity data and the respiration data over the period of time. In one embodiment, the data storage unit or memory is a standalone device. However, it is contemplated that the data storage unit or memory may be part of processor 208. In one embodiment, the stored data may be used for further processing, for example, for trending, and/or display. In such an embodiment, the data storage unit or memory of processor 208 may be in communication with the user interface 210 to display the stored data or the trend charts.

In one embodiment, system 200 may include user interface 210, which is in communication with the processor 208 and questionnaire system 206. The user interface 210 is configured to accept input from the patient (or caregiver), and optionally to transmit (and display) output of system 200.

In one embodiment, the user interface 210 may include a keyboard, keypad or touchscreen that allows the patient or caregiver to input the responses (i.e., clinical information of the patient) to the questions in the questionnaire. As noted above, clinical information of the patient may include information about respiratory symptoms of the patient, information about smoking history of the patient, and information about any other illnesses of the patient. In one embodiment, the respiratory symptoms may include cough, phlegm, breathlessness, wheezing and chest illnesses.

In one embodiment, user interface 210 may include a display screen that provides a visual data output (e.g., the assessed level of dyspnea (or dyspnea value) of the patient) to the patient. In one embodiment, user interface 210 may be a graphical user interface. It may also include a printer or be connected to a printer so as to be able to print information from processor 208. In one embodiment, a paper questionnaire is read to the patient, and the healthcare provider inputs one or more values into interface 210 based upon his or her assessment.

In one embodiment, user interface 210 may be provided integral with questionnaire system 206. In another embodiment, user interface 210 may be provided remote from or proximal to questionnaire system 206.

In one embodiment, processor 208 is configured to receive the clinical information stored in the data storage device (or memory) of questionnaire system 206. As noted above, this clinical information along with the data from the sensors (i.e., the activity monitor, and/or the respiration rate sensor) are used to assess the level of dyspnea in the patient.

In the system 200 shown in FIG. 2, separate sensors are used to measure the physical activity of the patient and the respiration rate of the patient. However, it is contemplated, that a single sensor may be used to measure the physical activity of the patient and the respiration rate of the patient as explained below.

FIG. 3 shows a system 300 that uses a single sensor for assessing the level of dyspnea in a patient (along with the clinical information from the questionnaire) in accordance with another embodiment of the present invention.

System 300 is configured for assessing the level of dyspnea in a patient by analyzing or processing the objectively assessed physical activity data, and respiration rate data over a period of time (e.g., the course of day), along with the clinical information of the patient. In one embodiment, the objective assessment is done using a single sensor, for example, an accelerometer (i.e., instead of the activity monitor 202 and the respiration rate sensor 204 as described above with respect to FIG. 2).

System 300 may include sensor 302, questionnaire system 306, processor 308, and user interface 310. In one embodiment, sensor 302 may be an accelerometer. In one embodiment, the accelerometer may be a three-axis accelerometer. Such an accelerometer may include a sensing element that is configured to determine acceleration data in at least three axes. For example, in one embodiment, the three-axis accelerometer may be a three-axis accelerometer (i.e., manufacturer part number: LIS3L02AQ) available from STMicroelectronics.

Figure 4:
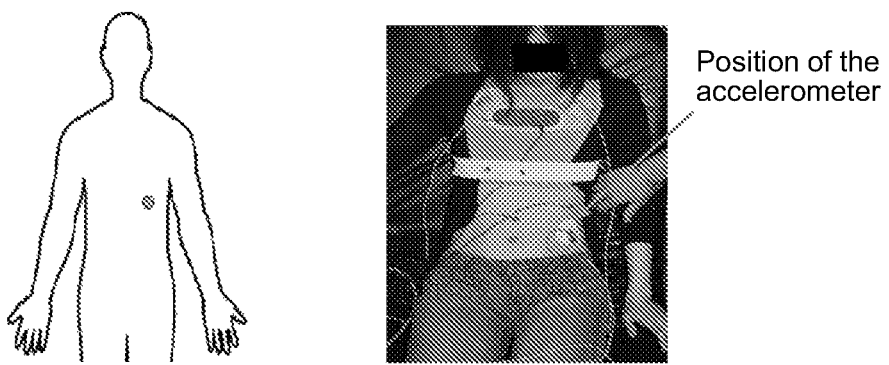
FIG. 4 shows the positioning of the accelerometer in accordance with an embodiment of the present invention.

In one embodiment, sensor 302 may be positioned, for example, at the thorax of the patient or at the abdomen of the patient. In one embodiment, as shown in FIG. 4, the accelerometer is positioned at the lower ribs, roughly halfway between the central and lateral position. The positioning of the accelerometer shown in FIG. 4 allows monitoring of both the respiration rate and the physical activity of the patient. In another embodiment, sensor 302 may be positioned such that sensor 302 is in close proximity with at least a portion of the patient's body.

In one embodiment, sensor 302 may be a part of a wearable band (that can be worn on the wrist, waist, arm or any other portion of the patient's body for example) or may be part of wearable garment worn by the patient.

In one embodiment, processor 308 of system 300 can comprise either one or a plurality of processors therein. Thus, the term "processor" as used herein broadly refers to a single processor or multiple processors. In one embodiment, processor 308 can be a part of or forming a computer system.

Processor 308 is configured to a) continuously receive acceleration data in at least the axes over a period of time; b) determine the respiration rate data from the accelerometer data; c) determine physical activity data associated with the respiration rate data; d) receive the clinical information of the patient from the questionnaire system 306; and e) process the respiration rate data, the physical activity data, and the clinical information of the patient to determine the dyspnea value for the patient. The dyspnea value is representative of the level of dyspnea in the patient.

In one embodiment, the period of time may be a course of a day. As noted above, the period of time may include a day, a week, a month, or any other desired time period. In one embodiment, the respiration rate may be determined intermittently over period of time (i.e., the course of day). In one embodiment, the respiration rate is measured during rest and predetermined activity level (e.g., moderate walk for more than 2 minutes).

In one embodiment, a segmentation algorithm may be used to determine the respiration rate from the accelerometer data. The segmentation algorithm is configured to select the periods during which the respiration rate may be determined.

In one embodiment, the segmentation of the data may be desirable necessary because it may not always be possible to determine the respiration rate reliably during the physical activity using an accelerometer (and/or other sensors). In one embodiment, the segmentation algorithm serves to automatically identify the periods of time during which the respiration rate can be determined reliably. In one embodiment, because the respiration rate doesn't immediately return to baseline values after an activity this is not a problem for the method.

In one embodiment, the respiration rate data measured for a predetermined length of time (e.g., about 20-30 seconds) is sufficient to determine the respiration rate reliably.

In one embodiment, the physical activity associated with this respiration rate value may then be the averaged over the last 5 minutes or 15 minute period rather than just that 20-30 seconds during which the respiration rate was calculated. In one embodiment, the physical activity in a 15-minute period preceding the time instances at which the respiration rate have been determined reliably Questionnaire system 306, processor 308, and user interface 310 of system 300 are similar to questionnaire system 206, processor 208, and user interface 210 of system 200 (shown and described in detail with respect to FIG. 2), and hence will not be explained in detail here.

Besides assessing the level of dyspnea in the patient, method 100 and systems 200 and 300 may be used in other circumstances where the simultaneous assessment of the physical activity, and the respiration rate may predict the onset of an exacerbation of a COPD patient In one embodiment, only an activity monitor (i.e., along with the questionnaires) is used to assess the level of dyspnea in the patient. In other words, questionnaires are used in addition to the activity monitoring as both a decrease in activity levels (or a constant activity level) in combination with clinical information obtained from the questionnaires provides information to assess the level of dyspnea in the patient.

In one embodiment, only a respiration rate monitor (i.e., along with the questionnaires) is used to assess the level of dyspnea in the patient. In one embodiment, trends in respiration rate are compared with the baseline respiration rate measurements to provide an indication of what constitutes as a significant increase in respiration rate. In such an embodiment, this increase should also remain relatively constant for a predetermined length of time. In other words, questionnaires are used in addition to the respiration rate monitoring as both an increase in respiration rate levels in combination with clinical information obtained from the questionnaires provides information to assess the level of dyspnea in the patient.

In one embodiment, the acquired measurements (i.e., the physical activity data over the period of time, and/or the respiration data over a period of time) along with the clinical information from the questionnaires may be used to calculate a single value, for example, a dyspnea risk score. The dyspnea risk score may be used in Early Warning Scoring Systems, for example, used by Rapid Response Teams. The dyspnea risk score may be used in the Early Warning Scoring Systems along with other known risk factors for deterioration, such as pulse rate, for example.

In one embodiment, systems 200 and 300 may each include a single processor that may be configured to process the respiration rate data, the physical activity data, and the clinical information of the patient to determine the dyspnea value for the patient. The dyspnea value is representative of the level of dyspnea in the patient.

In another embodiment, systems 200 and 300 may each include multiple processors, where each processor is configured to perform a specific function or operation. In such an embodiment, the multiple processors may be configured to process the respiration rate data, the physical activity data, and the clinical information of the patient to determine the dyspnea value for the patient. The dyspnea value is representative of the level of dyspnea in the patient.

In one embodiment, method 100 and systems 200 and 300 may be used in a rehabilitation center (e.g., for COPD patients, or heart failure patients). In one embodiment, method 100 and systems 200 and 300 may also be applied for home rehabilitation to enable patient assessment and intervention to be provided remotely.

Embodiments of the invention, the processor, for example, may be made in hardware, firmware, software, or various combinations thereof. The invention may also be implemented as instructions stored on a machine-readable medium, which may be read and executed using one or more processors. In one embodiment, the machine-readable medium may include various mechanisms for storing and/or transmitting information in a form that may be read by a machine (e.g., a computing device). For example, a machine-readable storage medium may include read only memory, random access memory, magnetic disk storage media, optical storage media, flash memory devices, and other media for storing information, and a machine-readable transmission media may include forms of propagated signals, including carrier waves, infrared signals, digital signals, and other media for transmitting information. While firmware, software, routines, or instructions may be described in the above disclosure in terms of specific exemplary aspects and embodiments performing certain actions, it will be apparent that such descriptions are merely for the sake of convenience and that such actions in fact result from computing devices, processing devices, processors, controllers, or other devices or machines executing the firmware, software, routines, or instructions.

Although the invention has been described in detail for the purpose of illustration, it is to be understood that such detail is solely for that purpose and that the invention is not limited to the disclosed embodiments, but, on the contrary, is intended to cover modifications and equivalent arrangements that are within the spirit and scope of the appended claims. In addition, it is to be understood that the present invention contemplates that, to the extent possible, one or more features of any embodiment may be combined with one or more features of any other embodiment.

What is claimed is:

1. A computer-implemented method for assessing a level of dyspnea in a patient, the method comprising:
    measuring physical activity of the patient over a period of time with an activity monitor to gather physical activity data;
    measuring respiration rate of the patient over the period of time with a respiration rate sensor to gather respiration rate data;
    administering, with a computer processor, a questionnaire to gather clinical information of the patient;
    determining, with the computer processor, a first baseline parameter reflecting a respiration rate of the patient at rest based on the respiration rate data and/or the physical activity data;
    determining, with the computer processor, a second baseline parameter reflecting a respiration rate of the patient during activity based on the respiration rate data and/or the physical activity data; and
    determining, with the computer processor, a dyspnea value for the patient based on the first baseline parameter, the second baseline parameter, and the clinical information of the patient, the dyspnea value being representative of the level of dyspnea in the patient, and wherein the dyspnea value is determined such that responsive to the measured respiration rate being greater than a sum of the respiration rate at rest and a first predetermined constant, and the physical activity level of the patient being lower than a predetermined activity level, the dyspnea value indicates the patient is experiencing dyspnea.

2. The method of claim 1, wherein the activity monitor is an accelerometer or a piezoelectric sensor.

3. The method of claim 2, wherein the activity monitor is an accelerometer, and wherein the accelerometer also constitutes the respiration rate sensor.

4. The method of claim 1, wherein the respiration rate sensor is an accelerometer or a microphone.

5. The method of claim 1, wherein the clinical information includes information about respiratory symptoms of the patient, information about smoking history of the patient, and information about any other illnesses of the patient.

6. The method of claim 1, wherein the dyspnea value is determined such that:
    responsive to the measured respiration rate being between a sum of the respiration rate during activity and a second predetermined constant, and a difference between the respiration rate during activity and the second predetermined constant; and the physical activity of the patient being low; the dyspnea value indicates the patient is not experiencing dyspnea.

7. A system for assessing a level of dyspnea in a patient, the system comprising:
    at least one sensor configured to measure a respiration rate of the patient to gather respiration rate data, and physical activity of the patient to gather physical activity data;
    a questionnaire system configured to gather clinical information of the patient; and
    a processor configured to:
        determine a first baseline parameter reflecting a respiration rate of the patient at rest based on the respiration rate data and/or the physical activity data;
        determine a second baseline parameter reflecting a respiration rate of the patient during activity based on the respiration rate data and/or the physical activity data; and
        process the first baseline parameter, the second baseline parameter and the clinical information of the patient to determine a dyspnea value for the patient, the dyspnea value being representative of the level of dyspnea in the patient, and wherein the dyspnea value is determined such that responsive to the measured respiration rate being greater than a sum of the respiration rate at rest and a first predetermined constant, and the physical activity level of the patient being lower than a predetermined activity level, the dyspnea value indicates the patient is experiencing dyspnea.

8. The system of claim 7, wherein the sensor is an activity monitor.

9. The system of claim 8, wherein the activity monitor is an accelerometer or a piezoelectric sensor.

10. The system of claim 7, wherein the sensor is a respiration rate sensor.

11. The system of claim 10, wherein the respiration rate sensor is an accelerometer or a microphone.

12. The system of claim 7, wherein the clinical information includes information about respiratory symptoms of the patient, information about smoking history of the patient, and information about any other illnesses of the patient.

13. The system of claim 7, wherein the processor is configured to determine the dyspnea value such that:
    responsive to the measured respiration rate being between a sum of the respiration rate during activity and a second predetermined constant, and a difference between the respiration rate during activity and the second predetermined constant, and the physical activity level of the patient being lower than a predetermined activity level the dyspnea value indicates the patient is not experiencing dyspnea.

14. A system for assessing a level of dyspnea in a patient, the system comprising:
means for measuring physical activity of the patient over a period of time to gather physical activity data;
means for measuring respiration rate of the patient over the period of time to gather respiration rate data;
means for administering a questionnaire to gather clinical information of the patient;
means for determining a first baseline parameter reflecting a respiration rate of the patient at rest based on the respiration rate data and/or the physical activity data;
means for determining a second baseline parameter reflecting a respiration rate of the patient during activity based on the respiration rate data and/or the physical activity data; and
means for determining a dyspnea value for the patient based on the first baseline parameter, the second baseline parameter, and the clinical information of the patient, the dyspnea value being representative of the level of dyspnea in the patient, and wherein the dyspnea value is determined such that responsive to the measured respiration rate being greater than a sum of the respiration rate at rest and a first predetermined constant, and the physical activity of the patient being lower than a predetermined activity level, the dyspnea value indicates the patient is experiencing dyspnea.

15. The system of claim 14, wherein the means for measuring physical activity includes a physical activity monitor, and wherein the physical activity monitor is an accelerometer.

16. The system of claim 14, wherein the means for measuring respiration rate include a respiration rate sensor, and wherein the respiration rate sensor is a microphone.

17. The system of claim 14, wherein the clinical information includes information about respiratory symptoms of the patient, information about smoking history of the patient, and information about any other illnesses of the patient.

18. The system of claim 14, wherein the dyspnea value is determined such that:
responsive to the measured respiration rate being between a sum of the respiration rate during activity and a second predetermined constant, and a difference between the respiration rate during activity and the second predetermined constant, and the physical activity level of the patient being lower than a predetermined activity level the dyspnea value indicates the patient is not experiencing dyspnea.

19. A computer-implemented method for assessing a level of dyspnea in a patient, the method comprising:
measuring physical activity of the patient over a period of time with an activity monitor to gather physical activity data;
measuring respiration rate of the patient over the period of time with a respiration rate sensor to gather respiration rate data;
administering, with a computer processor, a questionnaire to gather clinical information of the patient;
determining, with the computer processor, a first baseline parameter reflecting a respiration rate of the patient at rest based on the respiration rate data and/or the physical activity data;
determining, with the computer processor, a second baseline parameter reflecting a respiration rate of the patient during activity based on the respiration rate data and/or the physical activity data; and
determining, with the computer processor, a dyspnea value for the patient based on the first baseline parameter, the second baseline parameter, and the clinical information of the patient, the dyspnea value being representative of the level of dyspnea in the patient, and wherein the dyspnea value is determined such that responsive to the measured respiration rate being between a sum of the respiration rate during activity and a second predetermined constant, and a difference between the respiration rate during activity and the second predetermined constant, and the physical activity level of the patient being lower than a predetermined activity level, the dyspnea value indicates the patient is not experiencing dyspnea.

20. A system for assessing a level of dyspnea in a patient, the system comprising:
at least one sensor configured to measure a respiration rate of the patient to gather respiration rate data, and physical activity of the patient to gather physical activity data;
a questionnaire system configured to gather clinical information of the patient; and
a processor configured to:
determine a first baseline parameter reflecting a respiration rate of the patient at rest based on the respiration rate data and/or the physical activity data;
determine a second baseline parameter reflecting a respiration rate of the patient during activity based on the respiration rate data and/or the physical activity data; and
process the first baseline parameter, the second baseline parameter and the clinical information of the patient to determine a dyspnea value for the patient, the dyspnea value being representative of the level of dyspnea in the patient, wherein the processor is configured to determine the dyspnea value such that: responsive to the measured respiration rate being between a sum of the respiration rate during activity and a second predetermined constant, and a difference between the respiration rate during activity and the second predetermined constant, and the physical activity level of the patient being lower than a predetermined activity level, the dyspnea value indicates the patient is not experiencing dyspnea.

21. A system for assessing a level of dyspnea in a patient, the system comprising: means for measuring physical activity of the patient over a period of time to gather physical activity data;
means for measuring respiration rate of the patient over the period of time to gather respiration rate data;
means for administering a questionnaire to gather clinical information of the patient;
means for determining a first baseline parameter reflecting a respiration rate of the patient at rest based on the respiration rate data and/or the physical activity data;
means for determining a second baseline parameter reflecting a respiration rate of the patient during activity based on the respiration rate data and/or the physical activity data; and
means for determining a dyspnea value for the patient based on the first baseline parameter, the second baseline parameter, and the clinical information of the patient, the dyspnea value being representative of the level of dyspnea in the patient wherein the dyspnea value is determined such that:

responsive to the measured respiration rate being between a sum of the respiration rate during activity and a second predetermined constant, and a difference between the respiration rate during activity and the second predetermined constant, and the physical activity level of the patient being lower than a predetermined activity level, the dyspnea value indicates the patient is not experiencing dyspnea.

* * * * *